(12) United States Patent
Ikarashi et al.

(10) Patent No.: US 8,497,092 B2
(45) Date of Patent: Jul. 30, 2013

(54) METHOD OF BIOASSAYING YOKUKANSAN

(75) Inventors: Yasushi Ikarashi, Inashiki-gun (JP); Zenji Kawakami, Inashiki-gun (JP)

(73) Assignee: Tsumura & Co., Tokyo (JP)

( * ) Notice: Subject to any disclaimer, the term of this patent is extended or adjusted under 35 U.S.C. 154(b) by 259 days.

(21) Appl. No.: 12/936,282

(22) PCT Filed: Apr. 3, 2008

(86) PCT No.: PCT/JP2008/056684
§ 371 (c)(1),
(2), (4) Date: Oct. 4, 2010

(87) PCT Pub. No.: WO2009/122580
PCT Pub. Date: Oct. 8, 2009

(65) Prior Publication Data
US 2011/0027821 A1    Feb. 3, 2011

(51) Int. Cl.
*C12P 1/00* (2006.01)

(52) U.S. Cl.
USPC ............................................ 435/41; 435/325

(58) Field of Classification Search
USPC .................................................. 435/41, 325
See application file for complete search history.

(56) References Cited

U.S. PATENT DOCUMENTS

| | | | |
|---|---|---|---|
| 2003/0069201 A1 | 4/2003 | Reed | |
| 2004/0157850 A1 | 8/2004 | Kakihana et al. | |
| 2009/0098228 A1 | 4/2009 | Ikarashi et al. | |
| 2010/0196944 A1 | 8/2010 | Ikarashi et al. | |

FOREIGN PATENT DOCUMENTS

| | | |
|---|---|---|
| CN | 1616013 | 5/2005 |
| CN | 1739648 | 3/2006 |
| CN | 1939453 | 4/2007 |
| EP | 1 382 598 | 1/2004 |
| JP | 2000 512621 | 9/2000 |
| JP | 2001 521876 | 11/2001 |
| JP | 2003 176236 | 6/2003 |
| JP | 2003 313167 | 11/2003 |
| JP | 2005 520486 | 7/2005 |
| WO | 97 39355 | 10/1997 |
| WO | 99 20292 | 4/1999 |
| WO | 03 006686 | 1/2003 |

OTHER PUBLICATIONS

Mazzio et al. "Effect of antioxidants on L-glutamate and N-Methyl-4-Phenylpyridinium ion induced-neurotoxicity in PC12 cells", NeuroToxicology, 2001, 22:283-288.*
Iwasaki et al. "A randomized, observer-blind, controlled trial of the traditional Chinese medicine Yi-Gan San for improvement of behavioral and psychological symptoms and activities of daily living in dementia patients", J Clin Psychiatry, 2005, 66(2):248-252.*
U.S. Appl. No. 13/000,029, filed Dec. 20, 2010, Ikarashi, et al.
U.S. Appl. No. 12/539,153, filed Aug. 11, 2009, Tohyama, et al.
U.S. Appl. No. 12/867,514, filed Aug. 13, 2010, Ikarashi, et al.
Itoh, T., et al., "Efficacy of Choto-san on vascular dementia and the protective effect of the hooks and stems of *Uncaria sinensis* on glutamate-induced neuronal death," Mechanisms of Ageing and Development, vol. 111, pp. 155-173, (1999).
Shimada, Y., et al., "Evaluation of the Protective Effects of Alkaloids Isolated from the Hooks and Stems of *Uncaria sinensis* on Glutamate-induced Neuronal Death in Cultured Cerebellar Granule Cells from Rats," J. Pharm. Pharmacol., vol. 51, pp. 715-722, (1999).
Shimada, Y., et al., "Protective effect of *Uncaria sinensis* on glutamate-induced acute neuronal death in cultured rat cerebellar granule cells," Journal of Traditional Medicines, vol. 15, pp. 241-244, (1998).
Inanaga, K., "No to Kokoro no Oi Ninchisho no Kodo Shinri Jotai (BPS) no Yakubutsu Chiryo," Psychiatria Et Neurologia Japonica, vol. 109, No. 7, pp. 703-708, (2007).
Koh, I., et al., "A randomized, observer-blind, controlled trial of the traditional Chinese medicine Yi-Gan San for improvement of behavioral and psychological symptoms and activities of daily living in dementia patients," The Journal of Clinical Psychiatry, vol. 66, No. 2, pp. 248-252, Journal Code: 7801243, ISSN: 0160-6689, (Feb. 2005), (Abstract Only).
Hong, H., et al., "Scutellarin Attenuates Oxidative Glutamate Toxicity in PC12 Cells," Planta Med, vol. 70, pp. 427-731, (2004).
Yu, D., et al., "Isoflavonoids from *Astragalus mongholicus* protect PC12 cells from toxicity induced by L-glutamate," Journal of Ethnopharmacology, vol. 98, pp. 89-94, (2005).
Lee, J.-H., et al., "(-)-Epigallocatechin Gallate Attenuates Glutamate-Induced Cytotoxicity Via Intracellular $CA^{2+}$ Modulation in PC12 Cells," Clinical and Experimental Pharmacology and Physiology, vol. 31, pp. 530-536, (2004).
International Search Report issued May 1, 2008 in PCT/JP08/056684 filed Apr. 3, 2008.
Office Action and Search Report in corresponding Chinese Application No. 200880128344.3 issued Feb. 7, 2013.

* cited by examiner

*Primary Examiner* — Bin Shen
(74) *Attorney, Agent, or Firm* — Oblon, Spivak, McClelland, Maier & Neustadt, L.L.P.

(57) ABSTRACT

The invention intends to find out a bioassay system with an in-vitro test capable of ensuring the higher quality of yokukansan, and provides a bioassay method for yokukansan, comprising adding glutamate in an amount sufficient to induce cell death and yokukansan to a medium for culturing cells, and evaluating pharmacological activity value of yokukansan from viability of the cultured cells in the medium.

7 Claims, 3 Drawing Sheets

METHOD OF BIOASSAYING YOKUKANSAN

CONTINUING APPLICATION INFORMATION

This application is a National Stage of International Application No. PCT/JP08/056,684.

TECHNICAL FIELD

The present invention relates to an assay method for yokukansan, and more precisely, to an assay method capable of quantitatively evaluating the physiological activity level (pharmacological activity value) of yokukansan, a type of kampo preparation, by using cultured neuronal cells.

BACKGROUND ART

A kampo preparation is a pharmaceutical prepared by blending crude drugs, in which all the active ingredients are not always specifically identified. Furthermore, a single active ingredient alone does not always exhibit its effect, and some active ingredients may compositely act with each other. For securing its quality, it is said that an assay method capable of totally evaluating the whole kampo preparation is necessary (Patent Document 1, Patent Document 2).

The assay method includes a method of total evaluation by assaying the individual ingredients, and a bioassay of evaluating the physiological activity by using a biological material. The bioassay includes an in-vivo test and an in-vitro test, and the in-vivo test system has many limitations regarding the test facilities, test animals, processing capability, and the like, and there were some difficulties in applying the in-vivo test to the quality evaluation of kampo preparations.

On the other hand, the in-vitro test system does not require any special facilities and gives stable test results in a short period of time. For this reason, it is desired to establish a bioassay method with this system. In fact, for myostatin, a bioassay method is reported (Patent Document 3). However, for a kampo preparation that comprises a combination of crude drugs each having plural active ingredients by themselves, a suitable bioassay system could not always be found out, and the establishment of the bioassay system is desired.

For example, yokukansan, a type of kampo preparation, generally has the composition shown below. A suitable bioassay system is not yet found out also for yokukansan. For securing higher quality for yokukansan, the development of the bioassay system for yokukansan is desired.

TABLE 1

| Ingredients | Amount |
| --- | --- |
| JP *Atractylodes Lancea* Rhizome | 4.0 g |
| JP *Poria Sclerotium* | 4.0 g |
| JP Cnidium Rhizome | 3.0 g |
| JP Japanese Angelica Root | 3.0 g |
| JP Bupleurum Root | 2.0 g |
| JP Glycyrrhiza | 1.5 g |
| JP Uncaria Hook | 3.0 g |

Patent Document 1: JP-T 2000-512621
Patent Document 2: JP-T 2001-521876
Patent Document 3: JP-T 2005-520486
Non-Patent Document 1: "Planta Med." 2004 May; 70(5): 427-31 (Hong H, Liu G Q. Scutellarin attenuates oxidative glutamate toxicity in PC12 cells)
Non-Patent Document 2: "J. Ethnopharmacol." 2005 Apr. 8; 98(1-2): 89-94 (Yu D, Duan Y, Bao Y, Wei C, An L. Isoflavonoids from Astragalus mongholicus protect PC12 cells from toxicity induced by L-glutamate)
Non-Patent Document 3: "Clip. Exp. Pharmacol. Physiol." 2004 August; 31(8): 530-6 (Lee J H, Song D K, Jung C H, Shin D H, Park J, Kwon T K, Jang B C, Mun K C, Kim S P, Suh S I, Bae J H, (−)-Epigallocatechin gallate attenuates glutamate-induced cytotoxicity via intracellular Ca modulation in C12 cells)

DISCLOSURE OF THE INVENTION

Problems that the Invention is to Solve

Accordingly, an object of the present invention is to find out a bioassay system with an in-vitro test for yokukansan that can secure higher quality of the kampo preparation.

Means for Solving the Problems

Based on the idea that the yokukansan may exert directly protective action against glutamate-induced cell death as one of its functions, the present inventors have intensively conducted studies. As a result, they have confirmed that when cultured neuronal cells which are generally used in studies related to cell death are cultured in the presence of glutamate to induce cell death and at the same time, yokukansan is added, the cell death is inhibited in a dose-dependent manner. The inventors have found that application of this finding may construct a bioassay method for yokukansan against neuronal cell death, and thus the present invention has been completed.

Specifically, the present invention is directed to a bioassay method for yokukansan, comprising adding glutamate in an amount sufficient to induce cell death and yokukansan to a medium for culturing cells, and evaluating the pharmacological activity value of yokukansan from the viability of the cultured cells in the medium.

Effects of the Invention

According to the bioassay method of the present invention, the physiological activity level (pharmacological activity value) of yokukansan can be determined simply and stably by using an in-vitro test without limitation on the test facilities, test animals, the processing capability, and the like.

BEST MODE FOR CARRYING OUT THE INVENTION

The bioassay method for yokukansan of the present invention comprises adding glutamate in an amount sufficient to induce cell death and yokukansan to a medium for culturing neuronal cells, and evaluating the pharmacological activity value of yokukansan from the viability of the cultured neuronal cells in the medium.

In the bioassay method for yokukansan of the present invention, any cells known as allogenic cells can be used as the cultured neuronal cells. However, PC12 cells derived from a rat adrenal pheochromocytoma cell line are preferably used. In general, the PC12 cells are widely used in the study of cell death, and characteristically respond to a neurotrophic factor (nerve growth factor: NGF). When the PC12 cells are cultured in the absence of NGF, they show the phenotype of adrenal medullary chromaffin cells. On the other hand, when the PC12 cells are cultured in the presence of NGF, they extend long nerve fibers and differentiate into sympathetic ganglion-like cells. The PC12 cells are extremely versatile, and particularly as for the molecular biological application, enormous utilization thereof has been recorded. Further, in PC12 cells, cell death is caused by glutamate, however, it is known that the cell death is inhibited by plant-derived substances such as scutellarin, isoflavonoids, and (−)-epigallocatechin gallate (Non-Patent Documents 1 to 3).

PC12 cells to be used in the present invention can be prepared by culturing the cells in RPMI 1640 medium supplemented with 5% fetal bovine serum and 10% inactivated horse serum in a collagen-coated flask for a given period, for example, for 3 to 7 days.

While PC12 cells respond to a neurotrophic factor (nerve growth factor: NGF), cell death in PC12 cells is caused by glutamate in a concentration-dependent manner, regardless of whether NGF stimulation is present. Therefore, the presence or absence of NGF stimulation of PC12 cells does not affect the implementation of the present invention.

In the bioassay method for yokukansan of the present invention, the concentration of glutamate in a medium for culturing neuronal cells should be sufficient to induce cell death in these cultured cells. At the same time, however, addition of glutamate at a high concentration may cause an acid shift in pH of the medium, and thereby inducing cell death with a change in culture environment. Accordingly, it is necessary to select a condition where cell death can be induced by glutamate at a lower concentration.

Specifically, it is necessary to study the effect of serum, in consideration of the fact that glutamate is present in serum, which affects the viability of neuronal cells. Further, in neuronal cells culture, a culture container is generally coated with an extracellular matrix (such as collagen or polylysine) in order to increase adhesion of the cells to the container, and therefore, it is necessary to study such a substance to find out a better material. In addition to these, phenol red to be used as a medium additive has an estrogenic activity and thereby may affect the measurement of absorbance or fluorescence in some cases. Therefore, a study of the substance is also needed.

As the best condition for inducing cell death selected through these studies, a medium with dialyzed serum and without phenol red, and a plate coated with collagen are used. However, the implementation of the bioassay method of the present invention is not limited to such a condition.

In the present invention, the concentration of glutamate in the medium for effectively inducing cell death is preferably from 1 μM to 50 mM, more preferably from 1 mM to 20 mM.

One embodiment of the evaluation method using the bioassay of the present invention is a method in which cell death in PC12 cells is induced in a medium to which glutamate in an amount sufficient to induce cell death and a given amount of yokukansan are added, the number of viable cells are measured by the MTT assay method, and the pharmacological activity value of yokukansan is evaluated from the measurement.

The MTT assay method utilizes the fact that 3-(4,5-dimethylthiazol-2-yl)-2,5-diphenyltetrazolium bromide (MTT) is a substrate for mitochondrial dehydrogenase, and the higher viability a cell has, the larger amount of MTT is reduced, thereby the amount of yellow colored to red colored formazan produced by the reduction of MTT well corresponds to the number of viable cells. This method is capable of measuring only viable cells, and the absorbance of a sample at a wavelength of 570 nm is measured with a reference wavelength of 690 nm. It is a matter of course that any other known method may be used as long as it is capable of measuring the number of viable cells.

In this measurement, it is generally preferred that plural samples, preferably at least three samples each containing yokukansan of known concentration are simultaneously measured, and the pharmacological activity value of yokukansan in these test samples is determined. However, so far as the condition is almost the same, a calibration curve previously prepared from samples each containing yokukansan of known concentration may be used for the determination.

As described above, the pharmacological activity value of yokukansan in cultured neuronal cells can be evaluated. The mechanism of this action is directly based on the action of yokukansan. Specifically, the present inventors found that yokukansan inhibits cell death induced by glutamate in cultured neuronal cells, and based on this finding, it has become possible to evaluate the pharmacological activity value of yokukansan for inhibition of cell death.

Further, a standard preparation which has been clinically confirmed to have a pharmacological effect as yokukansan and a test preparation are evaluated for the pharmacological activity value under the same condition according to the bioassay method of the present invention, and the standard preparation and the test preparation are compared with each other, thereby the quality equivalence of the preparation can be evaluated.

Additionally, plural lots of preparations are evaluated for the pharmacological activity value according to the bioassay method of the present invention, and based on the uppermost and lowermost ranges derived from the mean data of the evaluation for the pharmacological activity value and the like, the pharmacological activity values of the test samples are evaluated as to whether or not they fall within the ranges, thereby the quality equivalence of the test preparations can also be evaluated.

EXAMPLES

The present invention is described in more detail with reference to the following Examples. However, the invention should not be whatsoever restricted at all by these Examples.

Example 1

Culture of PC12 Cells

PC12 cells (supply source: Dainippon Sumitomo Pharma Co., Ltd.) were cultured as follows. A flask having a culture area of 75 cm$^2$ was coated with collagen (a collagen acidic solution IAC-15, manufactured by Koken Co., Ltd.). An antibiotic-containing medium obtained by adding 5 mL of a penicillin-streptomycin solution (GIBCO 15070-063) to 500 mL of RPMI 1640 medium (GIBCO 22400-089), 5% fetal bovine serum (FBS; ICN 2916754), and 10% inactivated horse serum (HS; GIBCO 26050) were put in the flask to prepare a growth medium. After cryopreserved PC12 cells were thawed, the thawed PC12 cells were cultured in the growth medium for 1 week or more. The thus-obtained cultured cells were used in an experiment. Here, PC12 cells were subcultured by a mechanical detachment method using a Pasteur pipette and a syringe. All the cells used in the Examples were cultured in a $CO_2$ incubator at 37° C. in air containing 5% $CO_2$.

Example 2

Induction of Cell Death by Glutamate

By using PC12 cells obtained in Example 1, a culture condition to efficiently induce cell death by glutamate was studied as follows.

(1) Serum

The effect of serum on glutamate-induced cell death was studied. In comparison between normal serum (FBS and HS) and dialyzed serum (serum obtained by dialysis through an ultrafilter having an exclusion limit of 10000 daltons), a significant difference in the effect of serum on glutamate-induced cell death was not observed, however, dialyzed serum showed a greater tendency to induce cell death. The result is shown in FIG. 1.

(2) Coating

A cell matrix to facilitate the adhesion of PC12 cells to a culture plate was searched for, and the study was performed for three kinds of culture plates which are coated with collagen, poly-L-lysine (SIGMA P4707, molecular weight: 70,000 to 150,000), and Primaria (registered trademark) (a plate for primary culture in which a nitrogen-containing cation has been added to the surface thereof), respectively. The microscopic observation revealed that aggregated cells floated and the number of cells decreased due to weak cell adhesion in the plates of poly-L-lysine and Primaria (registered trademark). The result of measurement of viable cells by the MTT assay method is shown in FIG. 2.

(3) Medium Additive

In order to facilitate the detection of cell death, an additive for the culture medium was studied. RPMI 1640 medium with phenol red and HEPES (GIBCO 22400-089) was designated as PR(+) and RPMI 1640 medium without phenol red and HEPES (GIBCO 11835-030) was designated as PR(−), and a comparison study was performed. As a result, cell death was more likely to be induced in the medium without phenol red. The result is shown in FIG. 3.

From the above studies, the best culture condition for inducing cell death by glutamate was determined as follows: the cells are seeded on a plate coated with collagen, and a medium supplemented with dialyzed serum and without phenol red is used as an induction medium. The induction medium contains an antibiotic-containing medium obtained by adding 5 mL of a penicillin-streptomycin solution to 500 mL of RPMI 1640 medium (GIBCO 11835-030), 5% dialyzed fetal bovine serum (GIBCO 26400-044), and 10% dialyzed horse serum (Biowest S090D).

Example 3

Bioassay for Yokukansan

PC12 cells were cultured as follows on the basis of the above (1) to (3) conditions.

PC12 cells were seeded on a 96-well plate coated with collagen at a cell density of 5000 cells/well and cultured in the induction medium for 3 days from the seeding. Glutamate at concentrations of from 1 mM to 20 mM was added 2 days after the seeding, respectively, to induce cell death.

After 24 hours from the above induction of cell death, 0.5% MTT solution (Dojindo 345-01821) was added in an amount of 20 μL per 100 μL of the medium in the above 96-well plate and cultured for 5 hours. Then, 100 μL of a stopping solution (10% SDS in 0.01 N HCl) was added thereto to stop the reaction. The crystals of formazan were dissolved using a pipette, and after leaving the solution overnight, the absorbance at a wavelength of 570 nm was measured with a reference wavelength of 690 nm using a spectrometer (Multiskan MCC/340, manufactured by Titertek, Inc.). Thereafter, the cell viability was calculated from the following calculation formula on the basis of the obtained absorbance. The result is shown in FIG. 4. The measurement value (% of control) is a value obtained by using the group without the addition of glutamate as the control.

$$\text{Cell viability (\%)}=[(As-Abs)/(Ac-Abc)]\times 100$$

In the formula, As represents the absorbance of the sample (a well containing the cells, the medium with the test substance, and the MTT solution);

Ac represents the absorbance of the negative control (a well containing the cells, the control medium, and the MTT solution);

Abs represents the absorbance of the blank of the sample (a well containing the medium with the test substance and the MTT solution); and Abc represents the absorbance of the blank of the negative control (a well containing the control medium and the MTT solution).

Subsequently, a glutamate concentration of 17.5 mM at which cell death was effectively induced in FIG. 4 was selected, yokukansan (TJ-54, manufactured by Tsumura & Co.) was added thereto, and inhibitory effect of TJ-54 on glutamate-induced cell death in PC12 cells was determined from the cell viability in the same manner as described above. It was shown that in PC12 cells, TJ-54 inhibits cell death in a concentration-dependent manner within the range of from 10 to 1,000 μg/ml. The result is shown in FIG. 5.

From these results, it was shown that TJ-54 inhibits the decrease in the MTT activity due to the addition of glutamate in a concentration-dependent manner (FIG. 5). Further, it was revealed that a bioassay system for yokukansan can be constructed by using a calibration curve of the concentration-dependent inhibitory effect of TJ-54 on cell death prepared on the basis of the cell death induced by 17.5 mM glutamate (FIG. 6).

INDUSTRIAL APPLICABILITY

According to the present invention, the pharmacological activity value of yokukansan can be determined simply and stably by using an in-vitro test without limitations on the test facilities, test animals, the processing capability, and the like.

Accordingly, as compared with the conventional method in which a predetermined component to be contained is subjected to an analysis, the invention makes it possible to secure the quality of yokukansan to a higher degree.

Figure 1:
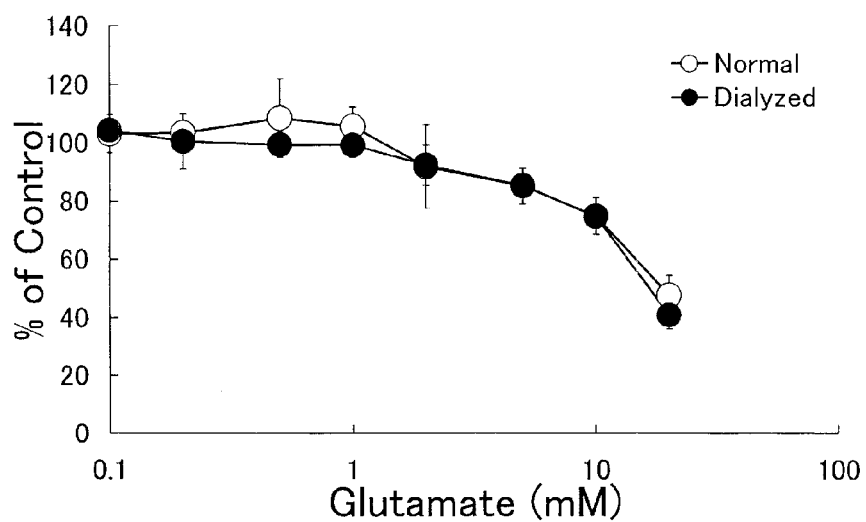
FIG. 1 is a view showing a relationship between the amount of glutamate and the cell viability when using normal serum and dialyzed serum. In the drawing, Normal denotes normal serum; and Dialyzed denotes dialyzed serum.
Figure 2:
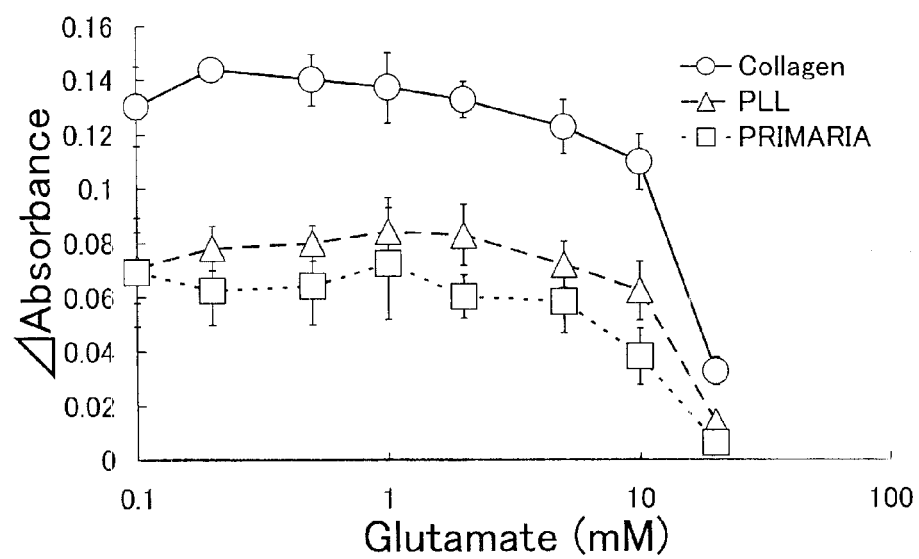
FIG. 2 is a view showing a relationship between the concentration of glutamate and the cell viability in three kinds of plates (collagen, poly-L-lysine, and Primaria (registered trademark)).
Figure 3:
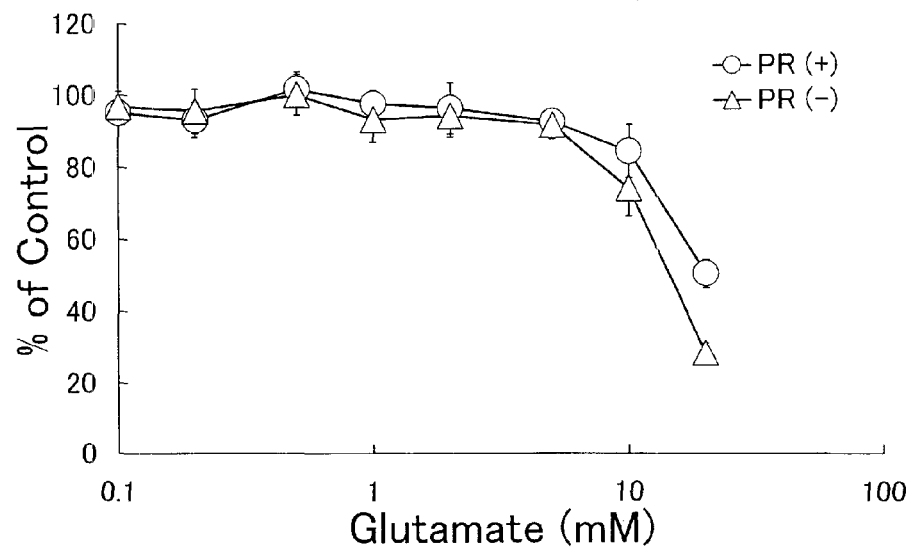
FIG. 3 is a view showing a relationship between the concentration of glutamate and the cell viability from the viewpoint of the presence or absence of a medium additive. In the drawing, PR(+) denotes RPMI 1640 medium with phenol red and HEPES; and PR(−) denotes RPMI 1640 medium without phenol red and HEPES.
Figure 4:
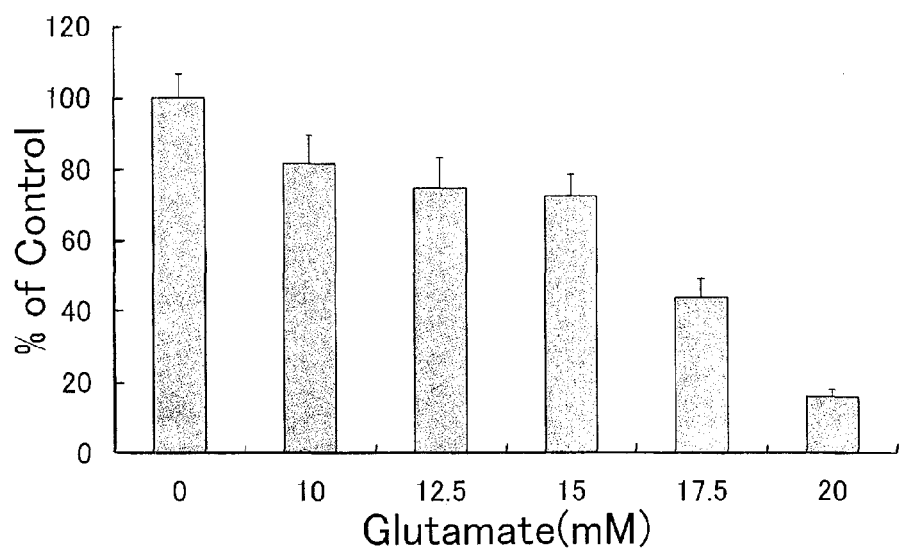
FIG. 4 is a view showing a relationship between the concentration of glutamate and the cell viability.
Figure 5:
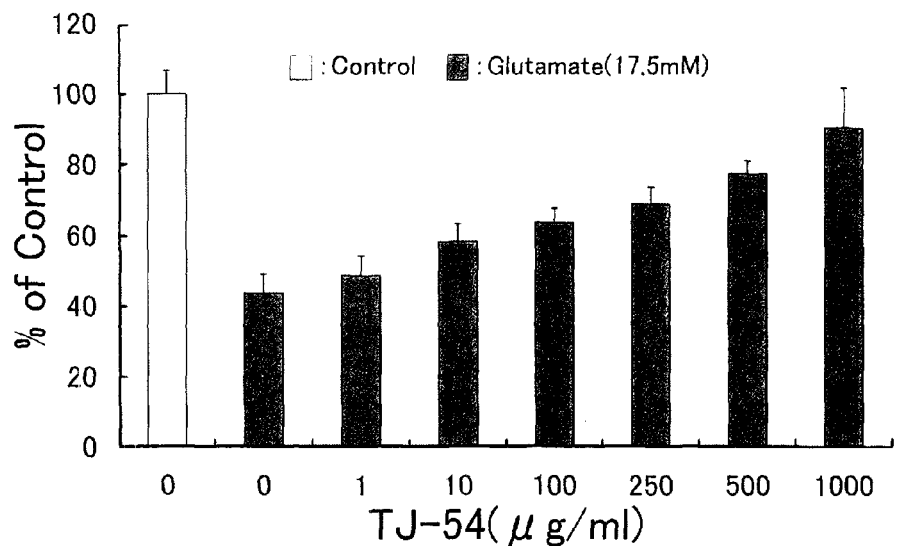
FIG. 5 is a view showing a relationship between the amount of TJ-54 and the cell viability in a medium containing glutamate at a concentration of 17.5 mM. In the drawing, Control denotes the cell viability without the addition of glutamate.
Figure 6:
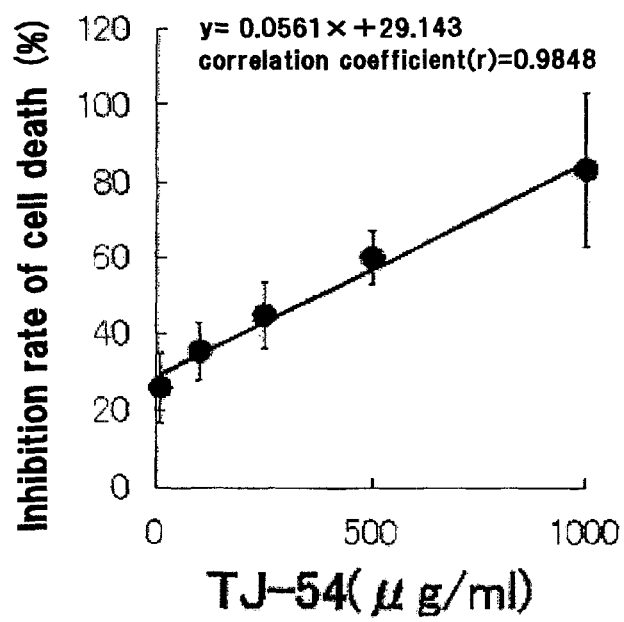
FIG. 6 is a calibration curve showing the concentration-dependent inhibitory effect of TJ-54 on glutamate-induced cell death prepared on the basis of the cell death induced by 17.5 mM glutamate from the results of FIG. 5.

The invention claimed is:

1. A bioassay method for yokukansan, comprising adding glutamate in a concentration sufficient to induce cell death and yokukansan to a medium containing cultured cells, and evaluating pharmacological activity value of yokukansan from viability of the cultured cells in the medium.

2. The bioassay method for yokukansan according to claim 1, wherein the cultured cells are cultured neuronal cells.

3. The bioassay method for yokukansan according to claim 1, wherein the cultured cells are PC12 cells.

4. The bioassay method for yokukansan according to any one of claim 1 or 2, wherein the concentration of glutamate in the medium for culturing the cells is from 1 µM to 50 mM.

5. The bioassay method for yokukansan according to claim 1, wherein the cultured cells are allogenic cells.

6. The bioassay method for yokukansan according to claim 1, wherein the concentration of glutamate in the medium for culturing the cells is from 1 mM to 20 mM.

7. The bioassay method for yokukansan according to claim 1, wherein the number of viable cells is measured by the MTT assay.

* * * * *